United States Patent [19]  [11] 4,441,509
Kotsifas et al.  [45] Apr. 10, 1984

[54] ENDOMETRIAL SAMPLING DEVICE

[75] Inventors: Peter N. Kotsifas, Lake St. Louis; Victor H. Wetzel, Bridgeton; Richard W. Gilson, Dellwood, all of Mo.

[73] Assignee: Sherwood Medical Company, St. Louis, Mo.

[21] Appl. No.: 265,763

[22] Filed: May 21, 1981

[51] Int. Cl.³ .......................... A61B 1/00; A61B 17/22
[52] U.S. Cl. ...................................... 128/757; 128/304
[58] Field of Search ............................... 128/751–758, 128/304

[56] References Cited

U.S. PATENT DOCUMENTS

| 1,867,624 | 7/1932 | Hoffman | 128/754 |
| 2,495,794 | 1/1950 | Weller | 128/2 |
| 3,438,366 | 4/1969 | Kariher et al. | 128/2 |
| 3,527,203 | 9/1970 | Gravlee | 128/2 |
| 3,769,980 | 11/1973 | Karman | 128/278 |
| 3,777,743 | 12/1973 | Binard et al. | 128/2 B |
| 3,889,657 | 6/1975 | Baumgarten | 128/2 B |
| 3,945,372 | 3/1976 | Milan et al. | 128/2 B |
| 3,955,579 | 5/1976 | Bridgman | 128/304 |

FOREIGN PATENT DOCUMENTS

| 2450597 | 11/1980 | France | 128/757 |
| 728852 | 5/1980 | U.S.S.R. | 128/753 |
| 2022421 | 12/1979 | United Kingdom . | |

OTHER PUBLICATIONS

Rocket of London Catalogue 1978, p. 107.

Primary Examiner—George F. Lesmes
Assistant Examiner—Nancy A. B. Swisher
Attorney, Agent, or Firm—Stanley N. Garber; Gregory E. Upchurch; William R. O'Mear

[57] ABSTRACT

An endometrial sampler is provided for obtaining an endometrial sample for clinical analysis which is safe to use and reduces patient discomfort. The sampler includes a handle and a flexible plastic probe having grooves on diametrically opposite sides adjacent the distal end of the probe. Each groove has a pair of sharp edges with each edge formed at the intersection of the periphery of the probe and a sidewall of the groove with the two forming an acute angle at their intersection. The probe is of solid plastic, relatively small in diameter and can be bent before insertion into the uterus of a patient to reduce patient discomfort.

7 Claims, 6 Drawing Figures

U.S. Patent  Apr. 10, 1984  4,441,509
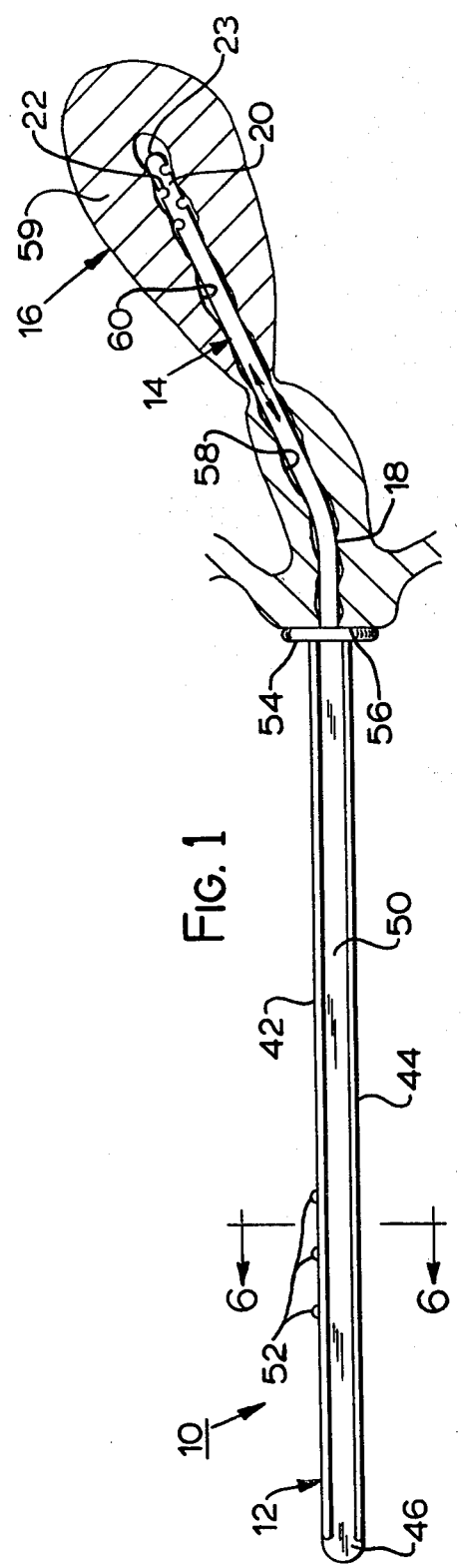
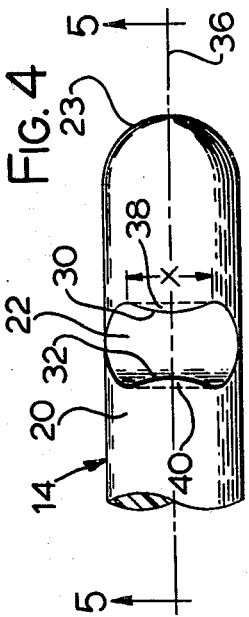
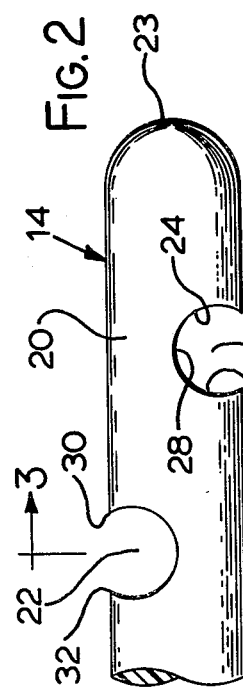
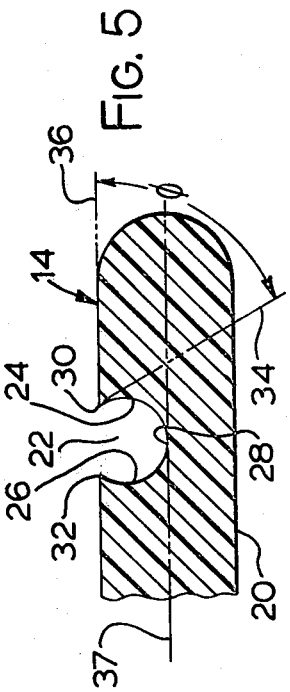
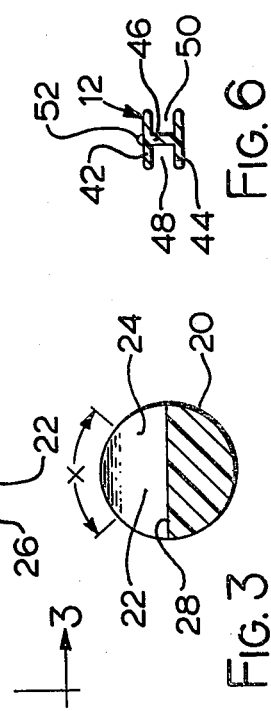

ENDOMETRIAL SAMPLING DEVICE

DESCRIPTION

1. Technical Field

This invention relates generally to medical sampling devices and more particularly to an endometrial sampling device for collecting endometrial sample material for clinical analysis.

2. Background Art

Sampling devices are used routinely in testing for uterine cancer. For example, in the well-known Pap smear test, a wooden paddle may be inserted into the vagina to a point near the opening to the cervix and then removed with a sample of cells and other matter remaining on the paddle. The sample is then subjected to cytological analysis. However, because endometrial cancer may be present in the upper regions of the uterus, it may go undetected even though a Pap test is performed.

Some sampling devices and methods have been proposed for collecting specimens from the uterus but have not been entirely satisfactory for one reason or another. It has been proposed to use a catheter for introducing a liquid into the uterus and then to withdraw the liquid and separate the sample material from the liquid for purposes of analysis. This method has the disadvantage that it runs the risk of causing abnormal cells to enter other passages, such as the fallopian tubes as well as requiring additional apparatus. In U.S. Pat. No. 3,527,203, a method is disclosed that includes irrigating the uterus with a liquid by means of a catheter and employing suction to the catheter to remove the liquid before it can move cells into the fallopian tubes. However, even if such methods are successful in preventing the spread of abnormal cells to other passages of the body, such methods require additional apparatus and the steps of removing the sample from the liquid, and then such methods provide a sample that is not in its natural state.

In U.S. Pat. No. 3,777,743, a sleeve is inserted into the cervix and a suction tube having a section with a plurality of holes, is moved from the sleeve into the body of the uterus. Suction applied to the proximal end of the tube assists movement of endometrial material into the interior of the tube through the holes. This method has the disadvantage that only relatively small amounts of sample material would usually be obtained because of the holes. Also, some loosened material is left in the uterus because of the withdrawal of the suction tube back into the sleeve. Furthermore, the outer diameter of the device inserted into the cervix is relatively large since telescoping tubes are used; and this would tend to result in greater discomfort to the patient.

In U.S. Pat. No. 3,438,366, a sleeve is inserted into the cervix and a rod with a piston slideable in the sleeve and provided with a probe is moved such that the probe enters the uterus body. A scraping edge at the end of the probe scrapes the endometrial material, and suction aids in drawing the material into the sleeve. In this arrangement, a limited amount of material is obtained because withdrawal of the rod into the sleeve tends to cause some scraped material to remain in the uterus. Also, this device requires a piston movable in a tube which results in a relatively large member that adds to patient discomfort.

In U.S. Pat. No. 3,945,372, a spiral section of a rod is inserted into the uterus and rotated in a specific direction to scrape and carry sample endometrial material. The material moves into the spiral section and when removed by rotation in the same specific direction carries with it the sample material. After removal of the spiral section from the patient, it is passed through a separate member having a slot which member collects the material from the spiral section for test purposes. A disadvantage of this device is that if an error is made in the direction of rotation of the spiral section, the spiral section will pick up little material. If the spiral rotation is in a correct direction during sample collection, improper rotation or rotation in the opposite direction upon removal will cause some of the material to move from the spiral section and remain within the patient.

In copending U.S. application Ser. No. 117,677, filed Feb. 1, 1980, assigned to the same assignee as this application, now U.S. Pat. No. 4,340,066 an endometrial sample collection device is provided which has a longitudinal slot. When rotated while in the uterus, the edges of the slot scrape the endometrium and sample material moves into the slot from both the upper and lower lateral sides of the uterus. In such case, the lateral side from which specific sample cells came cannot be determined because cells from both sides move into the same slot.

DISCLOSURE OF THE INVENTION

It is an object of the present invention to provide an improved endometrial sampling device which is economical to make, simple to use, capable of obtaining a desirable amount of sampling material from the endometrium, allows easy insertion, allows the easy removal of the sample material from the device for test purposes, reduces the chance of damage to the patient as well as reducing discomfort, and which substantially avoids or reduces one or more of the problems of the prior art devices.

In accordance with one aspect of the present invention, an endometrial sampler is provided which includes a handle and a flexible, solid plastic specimen collection probe having a groove adjacent the distal end of the probe. The groove has a scraping edge formed by the peripheral surface of the probe and a sidewall intersecting the peripheral surface at an acute angle.

These, as well as other objects and advantages of the present invention, will become apparent from the following detailed description and accompanying drawings.

BRIEF DESCRIPTION OF THE DRAWINGS

FIG. 1 is a side elevational view of an endometrial sampling device in accordance with a preferred embodiment of the present invention and is shown inserted into the uterus of a patient;

FIG. 2 is an enlarged side elevational view of a distal end portion of the sampling device of FIG. 1;

FIG. 3 is a cross-sectional view taken along line 3—3 of FIG. 2;

FIG. 4 is a plan view of a distal end portion of the sampling device shown in FIG. 2 but rotated 90°;

FIG. 5 is a cross-sectional view taken along line 5—5 of FIG. 4; and

FIG. 6 is a cross-sectional view taken along line 6—6 of FIG. 1.

DETAILED DESCRIPTION OF THE INVENTION

Referring now to the drawing, and particularly to FIG. 1, there is shown for illustration an endometrial sampler or specimen collecting device 10 having a handle 12 and an endometrial sampling collector probe or scraper 14 integrally connected to handle 12, and with the probe 14 inserted in the uterus 16 of a patient.

The probe 14 is formed of a suitable plastic such as a molded polyolefin, preferably polypropylene. Preferably, both handle 12 and probe 14 are molded as a single part. Probe 14 is an elongate rod circular in cross-section and solid throughout its length. It is preferably formed or molded with a bend as at 18 so that the distal portion of the probe is at an angle to the longitudinal axis of the handle. With this shape, the probe 14 more nearly conforms to the general anatomy making insertion and retraction from the uterus easier and with less discomfort to the patient. Since the anatomy varies with the patient, the preliminary examination can indicate how to pre-bend the probe 14 for easiest insertion. When formed of polypropylene, the probe 14 will tend to retain the shape into which it is bent.

The distal end portion 20 of probe 14 is provided with a plurality of specimen collecting grooves 22. As shown, there are four axially spaced grooves 22, although more or less grooves may be used. Two of the grooves 22 are shown on one side of probe 14 and the other two grooves are shown on the diametrically opposite side of the probe. The distal end or tip 23 of the probe is rounded or semi-spherical for safe, easy insertion.

As best seen in FIGS. 2–5, each groove 22 extends transversely across the probe 14, that is, the longitudinal axis of the groove is normal to the longitudinal axis of the probe. Each groove 22, as seen in FIG. 5., has axially spaced facing, opposed distal and proximal sidewalls 24 and 26, respectively, which are interconnected with a bottom wall 28. The walls 24 and 26 intersect the outer peripheral surface of the probe at an acute angle $\phi$ to provide sharp distal and proximal edges 30 and 32, respectively, at the periphery of the probe and mouth of the groove. The angle $\phi$ is indicated between a line 34 which is tangent to a portion of a circle defined in part by the surface of sidewall 24 at the point of intersection of sidewall 24 with the periphery of the probe, and a line 36 which is parallel with the longitudinal axis of the probe and is at the peripheral surface of the probe, and as seen in FIG. 4, crosses the center of groove 22.

Each of the grooves 22 in the illustrated embodiment are arcuate in cross-section (FIG. 5) and extends for more than 180° with the line 34 tangent to the arcuate surface of the sidewall 24 at the intersection with the periphery of the probe or line 36. Also, the longitudinal axis of the probe indicated at 37, is tangent to the arcuate surfaces of the grooves.

As shown in FIG. 4, the grooves 22 are shaped to provide facing overhang portions or hooks indicated at 38 and 40 which have the sharp edges 30 and 32, respectively, for scraping purposes. The edges 30 and 32 do not extend radially beyond the periphery of the probe but rather are formed at the intersection of the peripheral surface of the probe and the groove sidewalls 24 and 26. As apparent in FIGS. 2–4, the opposite ends of each of the grooves 22 are open and this facilitates removal of the collected endometrial sample material from the grooves onto a slide or specimen plate, as will be discussed hereafter.

As viewed in FIG. 4, the sharp edges 30 and 32 are rounded or generally arcuate, and are closest to each other at their centers which are along peripheral line 36. Each sharp edge smoothly curves, with respect to the probe, circumferentially and axially away from its center. The distal edge 30 curves distally from its center while the edge 32 curves proximally from its center. Since the overhanging portions 38 and 40 with their edges 30 and 32 extend circumferentially, they aid in holding collected sample material in the grooves. Also, since the mouth or width of the groove or distance between the edges 30 and 32 at line 36 is less than the maximum dimension of the groove below the periphery, the shape of the groove provides a good recepticle for collected material so that a substantial amount can be extracted from a patient.

The handle 12, as shown in FIGS. 1 and 6, includes upper and lower horizontal plates 42 and 44 and a central vertical plate 46 integrally connected to the upper and lower plates to provide finger recesses 48 and 50. Also, the handle 12 is provided with one or more bumps 52 on the upper horizontal plate 42. When held by the hand or fingers, the recesses 48 and 50, and bumps 52, provide an indication by feel of the orientation of the probe and grooves during insertion and while the probe 14 is in the patient. These feel indicators on the handle 12 facilitate insertion and retraction of the probe 14 during the taking of samples from the uterus and tend to reduce discomfort to the patient since the probe orientation relative to the uterus is known by the person taking the specimen.

In use, an initial pelvic examination may be desirable determine the size, position and configuration of the uterus of the patient from which endometrial scrapings or sample of tissue or cells is to be obtained. The probe 14 may then be bent, if necessary, to more nearly conform in shape to the shape that would cause the least discomfort to the patient.

The tip 23 of the probe 14 of sampler 10 is inserted through the cervical os 56, and where desired, with a probing action so as not to scrape the cervical walls indicated at 58, on entry of the probe. The handle 12 may then be moved inwardly of the patient until the stop member 54 engages the os. Under these conditions, the probe 14 is fully within the uterus 16 with the distal portion 20 within the body 59 of the uterus, and, preferably, in the orientation illustrated in FIG. 1. In this condition, the upper two grooves 22 face the upper lateral side of the uterus while the two lower grooves 22 face the lower lateral side of the uterus, as seen in FIG. 1. The handle recesses 46 and 48 and bumps 52 will aid in inserting and maintaining the probe in a desired orientation.

With the sampler 10 disposed in uterus 16, as illustrated in FIG. 1, a mild pressure may be applied to handle 12 in order to urge the probe 14 and scraping edges 30 and 32 of portions 38 and 40 of the upper two grooves 22 against the upper lateral side of the endometrial surface 60 of the body 59 of the uterus. With this pressure applied, the probe is moved linearly outwardly and inwardly (direction of arrow heads in FIG. 1) of the uterus. For example, three two-centimeter strokes may be performed so as to gently scrape the upper lateral portion of endometrial surface 60 to cause specimen material such as tissue and cells to be scraped by groove edges 30 and 32 into the upper two grooves 22. Then, exerting a mild pressure on handle 12 to urge the probe 14 and two grooves 22 in the bottom side of probe 14 and their scraping edges 30 and 32 against the lower lateral side of the endometrium or uterus body 59, the probe 14 may be linearly moved, for example, three two-centimeter strokes. The lower lateral surface will be scraped with a result that an endometrial sample including tissue and cells will enter the lower grooves 22. The probe may then be retracted from the uterus while maintaining the probe in a desired orientation.

Since the scraping edges 30 and 32 do not extend outwardly beyond the periphery of the probe and are rounded as opposed to being pointed, they do not cause damage or undue discomfort to the patient during linear movement of the probe in gathering the endometrial sample material.

After the sampler 10 is retracted from the patient, the probe 14, preferably with the longitudinal axis of the grooves 22 on one side of the probe parallel to the surface of the glass slide onto which the specimen material or sample is to be spread, is moved across or arcuately across the slide. The opposite ends of each groove 22 being open, the specimen material from those grooves readily moves in a direction normal to the longitudinal axis of the probe from the grooves to the plate where the material may be readily spread. The second plate, where desired, may be used to remove and spread the specimens from the grooves on the opposite side of the probe. In this way, the sample to be tested can be independently obtained from the upper and lower lateral sides of the body of the uterus. The material on the slides may then be treated and subjected to clinical testing in any suitable or conventional manner.

The stop member 54 may be formed where desired at an angle to the handle axis, that is, with the lower end, as viewed in FIG. 1, slightly distally of the upper end. With the stop member 54 tilted in such a manner, the pressures applied to the os may be evenly distributed on insertion of the sampler.

The bottom wall 28, and sidewalls 24 and 26 of each groove 22 intersect the peripheral surface of probe 14 at an angle of 90° except where the sidewalls intersect the periphery at an acute angle to form the sharp scraping edges 30 and 32. As used herein, a "sharp" edge means an edge formed by surfaces which intersect at an acute angle $\phi$ as opposed to an edge formed by surfaces that intersect an angle of 90° or greater.

The peripheral or arc length of each of the sharp scraping edges 30 and 32 of each groove 22 or arcuate distance between the ends of each sharp edge is indicated in FIGS. 3 and 4 by the peripheral or arcuate distance X. The distance X should be greater than 0.5 millimeter (mm) and is preferably greater than 1 mm. The larger the distance X for a given size probe 14, the greater will be the amount of material scraped by the device 10 and its ability to retain the material during removal of the probe from the patient. During movement of the probe in the patient, the overhanging portion 38 with edge 30 will tend to maintain material in the groove during retractile or proximal movement of the probe 14, while the overhanging portion 40 with edge 32 will tend to hold material in the groove during distal movement of the probe. Each of the sharp scraping edges of each groove 22 smoothly extends peripherally or circumferentially, that is, the edge does not form any point.

It is desirable to make the width or outer diameter of the probe 14 as small as possible in order to reduce discomfort during use. This is especially important in obtaining specimens from generally higher cancer risk, older females where some organ atrophy has taken place. However, the width or diameter of probe 14 must be large enough to provide a transverse groove 22 of sufficient size that it will hold enough sample material upon removal of the probe from the patient in order that desired clinical tests are possible. The probe 14 should have a width or outer diameter greater than 1 mm and preferably in the range of 1.5 to 6 mm. A preferred diameter for the probe is about 2.5 mm and with a groove or groves 22 having a depth of about one-half that of the outer diameter of the probe. Polypropylene provides a strong, flexible probe which can be provided with grooves such as shown in 22 in the drawing and still be strong enough to ensure against breaking.

In one desirable design, an endometrial sampler, made in accordance with the present invention, had a probe length from tip 23 to the stop 54 of approximately 9 centimeters. The probe 14 was made straight but at an angle of about 17° from the longitudinal axis of handle 12. The diameter of the probe was about 2.4 millimeters. The probe 14 has a substantially constant width or outer diameter throughout its length. Each of the edges had an arcuate length of about 1.8 mm. While the probe is preferably circular in cross-section other shapes, for example, oval may be used.

In making the device 10, the probe 14 may be molded by employing mold pins circular in cross-section to form the arcuate grooves 22. Such round mold pins are highly desirable since they have the least tendency to stick or to wear unevenly. However, the grooves may be formed to have other shapes. For example, the opposed proximal and distal sidewalls (24, 26) and bottom wall (28) could be made flat or of other shapes if desired, although arcuate grooves are preferred.

As various changes could be made in the above construction without departing from the scope of the invention, it is intended that all matter contained in the above description and apparatus shown in the accompanying drawing shall be interpreted as illustrative and not in a limiting sense.

We claim:

1. An endometrial sampler comprising an elongate, flexible, plastic specimen collection probe being solid in cross-section, and a handle connected to said probe for manually grasping the sampler and inserting said probe into the uterus of a patient and for retracting said probe from the uterus to obtain a specimen therefrom for clinical analysis, said probe having a groove therein adjacent the distal end thereof extending substantially normal to the longitudinal axis of said probe, said groove having a bottom wall and axially spaced opposed proximal and distal sidewalls, said distal sidewall intersecting the outer periphery of said probe at an acute angle to provide a sharp scraping edge at the periphery of said probe and having a distal sidewall portion extending proximally to overhang said groove, said edge extending circumferentially in a smoothly curving configuration, the minimum width of the mouth of said groove measured along a line parallel to the longitudinal axis of said probe being less than the maximum width dimension of the groove measured along a line parallel to the longitudinal axis of said probe.

2. The sampler of claim 1 wherein said proximal sidewall intersects the periphery of said probe at an acute angle to provide another sharp scraping edge at the periphery of said probe, said proximal sidewall having a proximal sidewall portion extending distally to overhang said groove.

3. The sampler of claim 1 wherein said probe is circular in cross-section.

4. The probe of claim 3 wherein said probe is formed of a polypropylene plastic and the outer diameter of said probe is less than 6 millimeters.

5. An endometrial sampler comprising an elongate, flexible, plastic specimen collection probe solid and generally circular in cross-section and having a constant diameter substantially throughout its length, and a handle connected to said probe for manually grasping the sampler and inserting said probe into the uterus of a patient and for retracting said probe from the uterus to obtain an endometrial specimen from the walls of the uterus for clinical analysis, said probe having at least one groove on each of the opposite sides thereof extending normal to the longitudinal axis of said probe, each of said grooves having a bottom wall and axially spaced, opposed proximal and distal sidewalls connected with said bottom wall, each of said distal sidewalls intersecting the outer periphery of said probe at an acute angle to provide a sharp scraping edge at the periphery of said probe, each of said distal sidewalls having a distal sidewall portion extending proximally to overhang the associated groove, said sidewalls and the bottom wall of each of said grooves connecting to form an arcuate surface, said arcuate surface being in the form of a portion of a circle when said probe is taken in longitudinal section along its longitudinal axis, and wherein said circle has a radius of greater length than the distance between the center of said circle and the closest point on an imaginary cylinder defined by the outer peripheral surface of said probe.

6. An endometrial sampler comprising an elongate, flexible, plastic specimen collection probe solid and generally circular in cross-section and having a constant diameter substantially throughout its length, and a handle connected to said probe for manually grasping the sampler and inserting said probe into the uterus of a patient and for retracting said probe from the uterus to obtain an endometrial specimen from the walls of the uterus for clinical analysis, said probe having at least one groove on each of the opposite sides thereof extending normal to the longitudinal axis of said probe, each of said grooves having a bottom wall and axially spaced, opposed proximal and distal sidewalls connected with said bottom wall, each of said distal sidewalls intersecting the outer periphery of said probe at an acute angle to provide a sharp scraping edge at the periphery of said probe, each of said distal sidewalls having a distal sidewall portion extending proximally to overhang the associated groove, each of said grooves being open at both of the opposite ends thereof with the bottom wall thereof being straight from one end to the other, the width of the mouth of each of said grooves at its smallest dimension at the periphery of said probe and as measured along a line parallel to the longitudinal axis of said probe is less than the maximum width dimension of the groove as measured along a line parallel to the longitudinal axis of said probe.

7. The sampler of claim 5 or 6 wherein each of said proximal sidewalls intersects the outer periphery of said probe at an acute angle to provide a sharp scraping edge at the periphery of said probe, each of said proximal sidewalls having a proximal sidewall portion extending distally to overhang the associated groove.

* * * * *